United States Patent [19]

Brode, II et al.

[11] Patent Number: 5,300,494
[45] Date of Patent: Apr. 5, 1994

[54] DELIVERY SYSTEMS FOR QUATERNARY AND RELATED COMPOUNDS

[75] Inventors: George L. Brode, II, Bridgewater; George A. Salensky, White House Station, both of N.J.

[73] Assignee: Union Carbide Chemicals & Plastics Technology Corporation, Danbury, Conn.

[21] Appl. No.: 378,837

[22] Filed: Jul. 12, 1989

Related U.S. Application Data

[63] Continuation-in-part of Ser. No. 268,871, Nov. 8, 1988, Pat. No. 4,946,870, which is a continuation-in-part of Ser. No. 189,312, Feb. 3, 1988, Pat. No. 4,929,722, which is a continuation-in-part of Ser. No. 871,381, Jun. 6, 1986, abandoned.

[51] Int. Cl.$^5$ ............... A01N 25/24; A01N 33/00; A01N 57/16; A61K 31/73
[52] U.S. Cl. .................. 514/55; 424/78.03; 424/78.07; 424/484; 514/94; 558/170
[58] Field of Search ............ 514/937, 54, 642, 55, 514/777.94; 424/488, 484, 78.03, 78.07; 536/20; 558/170

[56] References Cited

U.S. PATENT DOCUMENTS

| | | | |
|---|---|---|---|
| 2,072,771 | 5/1936 | Rigby | 536/20 |
| 3,632,754 | 1/1972 | Balassa | 514/55 |
| 3,950,541 | 4/1976 | Waldstein | 514/642 |
| 3,953,608 | 4/1976 | Vanlerberghe | 514/777 |
| 4,021,572 | 5/1977 | Van Scott | 514/557 |
| 4,076,799 | 2/1978 | Willer | 424/45 |
| 4,215,064 | 7/1980 | Lindemann et al. | 558/170 |
| 4,233,192 | 11/1980 | Lindemann et al. | 558/170 |
| 4,275,194 | 6/1981 | Kato et al. | 536/20 |
| 4,336,070 | 1/1982 | Koshugi | 536/20 |
| 4,365,050 | 12/1982 | Ivani | 527/312 |
| 4,402,977 | 9/1983 | Grollier et al. | 424/71 |
| 4,424,346 | 1/1984 | Hall et al. | 536/20 |
| 4,532,267 | 7/1985 | Allan | 523/106 |
| 4,533,540 | 8/1985 | Blank | 514/785 |
| 4,574,150 | 3/1986 | Austin | 536/20 |
| 4,613,502 | 9/1986 | Turkova | 514/55 |
| 4,659,700 | 4/1987 | Jackson | 514/55 |
| 4,726,945 | 2/1988 | Patel | 424/70 |
| 4,738,850 | 4/1988 | Thakur et al. | 424/468 |
| 4,760,079 | 7/1988 | Baldone | 514/642 |
| 4,767,463 | 8/1988 | Brode et al. | 106/162 |
| 4,772,689 | 9/1988 | Lang et al. | 424/70 |
| 4,772,690 | 9/1988 | Lang | 536/20 |
| 4,780,310 | 10/1988 | Lang | 536/20 |
| 4,804,492 | 2/1989 | Bernarducci | 514/642 |
| 4,810,489 | 3/1989 | Murray | 514/937 |
| 4,902,720 | 2/1990 | Baldone | 514/642 |
| 4,929,722 | 11/1990 | Partain et al. | 424/59 |
| 4,931,551 | 6/1990 | Albisetti et al. | 536/20 |
| 4,946,870 | 8/1990 | Partain et al. | 514/55 |

FOREIGN PATENT DOCUMENTS

| | | |
|---|---|---|
| 0013181 | 9/1980 | European Pat. Off. |
| 3027943 | 2/1981 | Fed. Rep. of Germany. |
| 54-011955 | 1/1979 | Japan. |
| 57-180602 | 11/1981 | Japan. |
| 60-1110 | 1/1985 | Japan. |
| 61-118401 | 6/1986 | Japan. |
| 62-249994 | 10/1987 | Japan. |
| 62-288602 | 12/1987 | Japan. |
| 63-225602 | 9/1988 | Japan. |
| 87/07618 | 12/1987 | PCT Int'l Appl. |
| 2055119 | 2/1981 | United Kingdom. |

OTHER PUBLICATIONS

Hexetidine brochure (4 pages).
Hexamethonium, Abstract No. 4582 at p. 678, Merck Index, 10th Ed.
Jurgens Advertisement (4 pages).

Primary Examiner—Jeffrey E. Russel
Attorney, Agent, or Firm—W. K. Volles

[57] ABSTRACT

The invention relates to a method for topical application of a pharmaceutically or therapeutically active agent through the use of a covalent chitosan derivative or chitosonium polymer. The present invention is particularly well suited for the topical delivery of pharmaceutically active quaternary ammonia compounds of the formula:

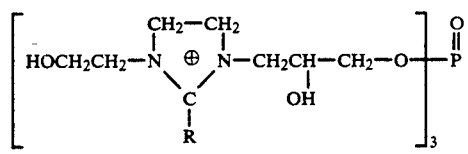

wherein R is alkyl having between 5 and 11 carbon atoms.

1 Claim, No Drawings

DELIVERY SYSTEMS FOR QUATERNARY AND RELATED COMPOUNDS

RELATED U.S. APPLICATION DATA

This application is a continuation-in-part of Ser. No. 268,871, filed Nov. 8, 1988, now U.S. Pat. No. 4,946,870, which is a continuation-in-part of Ser. No. 189,312 filed Feb. 3, 1988, now U.S. Pat. No. 4,929,722, which is a continuation of PCT US 87/001,246, filed Jun. 2, 1987, which is a continuation-in-part of Ser. No. 871,381, filed Jun. 6, 1986, now abandoned.

FIELD OF THE INVENTION

This invention relates to a method for topical application of a pharmaceutically or therapeutically active agent. The invention also relates to topical delivery systems for these active agents, which are useful as disinfectants (i.e., they have bactericidal and fungicidal activity).

BACKGROUND OF THE INVENTION

Traditionally, pharmaceutically and therapeutically active agent agents can be administered to the body by a number of routes, including ingestion, injection, inhalation, and topical application. Absorption of an active agent by ingestion, injection, or inhalation generally gives systemic distribution of the agent throughout the body. Systemic distribution of the agent may be unsatisfactory for three reasons. First, these modes of administration produce non-specific distribution. The active agent is distributed through the entire body and not localized. Second, there may be undesirable effects such as toxic or irritating reactions on non-target organs or regions. Finally, to achieve the desired effect at the target organ or region, a higher dosage than might otherwise be desired must be administered to compensate for systemic dilution of the active agent.

In contrast to systemic delivery, topical delivery is application of an active agent in a manner so that it acts primarily at the site of application. This type of application is used typically for dermatological disorders. The above-described deficiencies of systemic delivery are not encountered when an active agent is applied topically. Rather, topical application affords the opportunity to minimize the dosage and confine the active agent to the region of the body to which it is applied. Thus, systemic distribution of the agent throughout the body is obviated. For example, ingestion of acetone could cause fetal problems which dermal delivery should avoid. Typical sites of topical delivery include application to the dermal, opththalmic, and mucous membranes and tissues, such as the hair, skin, eyes, ears, mouth, nose, throat, rectum, vagina, and urethra.

However, despite these advantages of topical delivery, most current topical delivery formulations are inefficient and therefore have limited utility. There are four reasons for this inefficiency of current topical delivery technology. First, skin and mucous membranes possess good barrier properties and the permeability of most active agents through these barriers generally is poor. Second, active agents applied topically are subject to migration and loss due to perspiration, natural tissue lavation, and mechanical action. Third, because most pharmaceutically or therapeutically active agents are relatively simple, low molecular weight compounds or mixtures, these agents are not applied alone, but in combination with a variety of additives to deliver the active agent to the application site and control the dosage. Fourth, the choice of a proper delivery system can minimize undesirable crystallization of the active agent, and hence optimize its availability in its active form. Most known topical delivery systems are petrolatum-based cremes and ointments. These unetuous formulations are unsatisfactory because they are at best uncomfortable and messy when applied.

A topical delivery system cannot be considered fully satisfactory if it is deficient with regard to any of the above-described criteria. For example, a delivery system which does not ensure that the active agent efficiently penetrates the application site is not satisfactory because it requires that an excess of agent be incorporated into the delivery system to ensure delivery of an effective quantity. The remaining active agent, i.e., that which does not penetrate the application site, is wasted. Similarly, agent which is allowed to migrate from the application site, or to crystallize before it penetrates the site, is wasted. Further, a delivery system which satisfies each criterion will be adjudged a failure by a consumer who is dissatisfied because the delivery system leaves an unpleasant residue. For example, an unctuous residue, which is unpleasant to the touch and messy, may cause a consumer not to utilize the treatment. Thus, such delivery systems are unsatisfactory.

The advantages of topical application of active agents which are bacteriostatically or fungistatically active are manifest. It also is advantageous, as described above, to apply topically treatments for lesions which result from infections such as herpes virus (types 1 and 2). Such treatments are described in U.S. Pat. No. 4,381,296 and U.S. Pat. No. 4,760,079. The former discloses a suspension of tannic acid, boric acid, and salicylic acid as the active agent, while the latter discloses that tetraethylammonium ion inhibits herpes symptoms. However, each of these treatments is unsatisfactory because each utilizes a delivery system which does not ensure that the active agents are retained at the treatment site.

SUMMARY OF THE INVENTION

The method of the invention for topically delivering a pharmaceutically or therapeutically effective quantity of an active agent selected from the group consisting of compounds of the formula:

$$[N\ (R_1)\ (R_2)\ (R_3)\ (R_4)]^+ \qquad (I)$$

wherein each $R_1$, $R_2$, $R_3$, and $R_4$ is straight chain or branched alkyl, alkylene, alkylaryl, saturated or unsaturated heterocyclic, saturated or unsaturated heterocyclic hydroxyalkyl, hydroxyalkyl, or hydroxyalkylene having up to about 20 carbon atoms; compounds of the formula $$[(R_5)\ (R_6)\ (R_7)\ N-(CH_{2n})-N\ (R_8)\ (R_9)\ (R_{10})]^{++} \qquad (II)$$

wherein each $R_5$, $R_6$, $R_7$, $R_8$, $R_9$, and $R_{10}$ is hydrogen or straight chain or branched alkyl, alkylene, alkylaryl, saturated or unsaturated heterocyclic, saturated or unsaturated heterocyclic hydroxyalkyl, hydroxyalkyl, or hydroxyalkylene having up to about 10 carbon atoms; and n is between 1 and about 10; compounds of the formulae

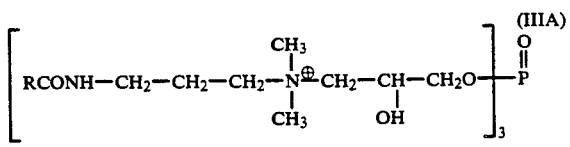

and

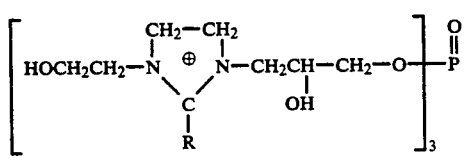

wherein R is alkyl having from 5 to 17 carbon atoms; and 5-amino-1,3-bis(2-ethylhexyl)-5-methylhexahydropyrimidene and biologically acceptable salts thereof; and blends thereof; said method comprising applying to the topical site a biocompatible, substantive, film-forming system for delivering the active agent, said system comprising the active agent and at least one aminopolysaccharide derivative selected from the group consisting of chitosonium polymers and covalent chitosan derivatives.

The delivery system of the present invention comprises a biocompatible, substantive, film-forming system for the delivery of pharmaceutically or therapeutically active agents to a desired topical site of a subject or host. The system comprises (a) at least one aminopolysaccharide derivative selected from the group consisting of chitosonium polymers and covalent chitosan derivatives; and (b) a pharmaceutically or therapeutically effective quantity of an active agent selected from the group consisting of compounds of the formula:

$$[N(R_1)(R_2)(R_3)(R_4)]^+ \quad (I)$$

wherein each $R_1$, $R_2$, $R_3$, and $R_4$ is straight chain or branched alkyl, alkylene, alkylaryl, saturated or unsaturated heterocyclic, saturated or unsaturated heterocyclic hydroxyalkyl, hydroxyalkyl, or hydroxyalkylene having up to about 20 carbon atoms; compounds of the formula $$[(R_5)(R_6)(R_7)N-(CH_{2n})-N(R_8)(R_9)(R_{10})]^{++} \quad (II)$$

wherein each $R_5$, $R_6$, $R_7$, $R_8$, $R_9$, and $R_{10}$ hydrogen or straight chain or branched alkyl, alkylene, alkylaryl, saturated or unsaturated heterocyclic, saturated or unsaturated heterocyclic hydroxyalkyl, hydroxyalkyl, or hydroxyalkylene having up to about 10 carbon atoms; and n is between 1 and about 10; compounds of the formulae

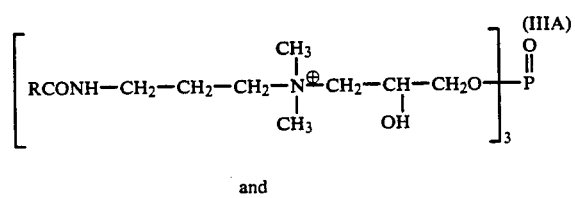

and

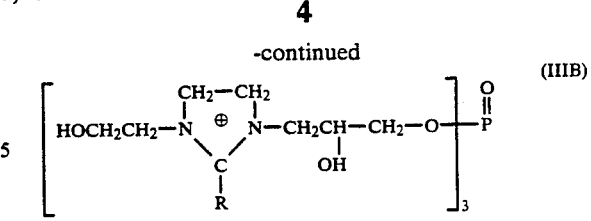

wherein R is alkyl having from 5 to 17 carbon atoms; 5-amino-1,3-bis(2-ethylhexyl)-5-methylhexahydropyrimidine and biologically acceptable salts thereof; and blends thereof.

The system efficiently delivers the active agents to the user at the application site and provides at the site a non-irritating, essentially imperceptible, substantive, gas permeable film over the application site.

DETAILED DESCRIPTION OF THE INVENTION

This invention is based on the discovery that a delivery system comprising an aminopolysaccharide derivative and a pharmaceutically or therapeutically active agent safely and effectively delivers these agents topically.

As an example, 5-amino-1,3-bis(2-ethylhexyl)-5-methylhexahydropyrimidene has known antifungal and antibacterial properties, and quaternary ammonium compounds are known bacteriostats. Further, as described above, tetraethylammonium ion is known to have efficacy against such herpes virus-caused diseases, but a satisfactory delivery system was not known, until disclosed in this specification.

As used throughout the specification and claims, the phrase "pharmaceutically active agent" is considered to be a drug, i.e., a substance which, when applied to the body, alters body functions in some way. The phrase "therapeutically active agent" is broader in scope and includes any substance which is capable of altering either body function or cosmetic appearance or which acts as an anaesthetic, but which is not traditionally or technically considered a drug.

It has been discovered that compounds of the formula $$[N(R_1)(R_2)(R_3)(R_4)]^+ \quad (I)$$

wherein each $R_1$, $R_2$, $R_3$, and $R_4$ is straight chain or branched alkyl, alkylene, alkylaryl, saturated or unsaturated heterocyclic, saturated or unsaturated heterocyclic hydroxyalkyl, hydroxyalkyl, or hydroxyalkylene having up to about 20 carbon atoms; compounds of the formula $$[(R_5)(R_6)(R_7)N-(CH_{2n})-N(R_8)(R_9)(R_{10})]^{++} \quad (II)$$

wherein each $R_5$, $R_6$, $R_7$, $R_8$, $R_9$, and $R_{10}$ is hydrogen or straight chain or branched alkyl, alkylene, alkylaryl, saturated or unsaturated heterocyclic, saturated or unsaturated heterocyclic hydroxyalkyl, hydroxyalkyl, or hydroxyalkylene having up to about 10 carbon atoms; and n is between 1 and about 10; compounds of the formulae

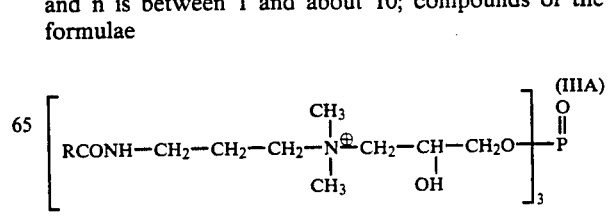

-continued

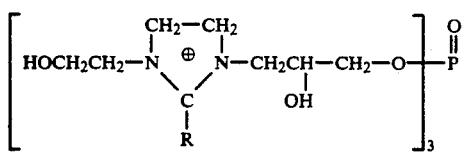

wherein R is alkyl having from 5 to 17 carbon atoms; and 5-amino-1,3-bis(2-ethylhexyl)-5-methylhexahydropyrimidene and biologically acceptable salts thereof; and blends thereof, can be topically applied as part of a delivery system comprising the active agent and an aminopolysaccharide derivative.

The compounds of formulae I, II, IIIA, and IIIB are quaternary ammonium and related ions. These cations exist in association with counter-ions, i.e., negatively-charged ions. Skilled practitioners recognize that these counter-ions can be any suitable biosafe anion. For example, suitable anions include the halides, carbonate, bicarbonate, sulfate, ethyl sulfate, lactate, and other anions which form organic and mineral acids. Preferably, the counter-ions are halides.

The compounds of formulae IIIA and IIIB are products sold under the trade name MONAQUAT, and are available with chloride as the counter-ions.

The compound 5-amino-1,3-bis(2-ethylhexyl)-5-methylhexahydropyrimidene forms salt with organic and mineral acids. Any of the above-described biosafe salts, such as the halide, ethyl sulfate, and lactate, are suitable for use in the method of the invention. Preferably, the halides are utilized herein.

Preferably, $R_1$, $R_2$, $R_3$, and $R_4$ are selected to enhance penetration of the active agent through the skin. Therefore, preferably one of $R_1$, $R_2$, $R_3$, or $R_4$ is a straight chain alkyl, alkylene, hydroxyalkyl, or hydroxyalkylene having between six and 20, more preferably between 6 and about 10, carbon atoms, while the remaining three of $R_1$, $R_2$, $R_3$, and $R_4$ Preferably are straight chain alkyl, alkylene, hydroxyalkyl, or hydroxyalkylene having between one and ten carbon atoms, more preferably between about one and five carbon atoms.

The straight chain alkyl or hydroxyalkyl moiety is compatible with the carbohydrates and amino acids such as tropocollagen in the interstices of the skin between the lipid bilayer/keratin structures, and will aid the penetration of the skin. Thus, the composition is favorably attracted to the phospholipids in the skin. The other moieties are small enough to penetrate the skin. A plurality of hydroxy-containing groups also aids penetration of the dermis.

Other preferred embodiments include those wherein each of $R_1$, $R_2$, $R_3$, and $R_4$ is a straight chain alkyl, alkylene, hydroxyalkyl, or hydroxyalkylene having up to about 5 carbon atoms, or benzyl.

Therefore, the preferred compounds of formula I are tris(hydroxymethyl)methylammonium, tetra(hydroxyethyl)ammonium, di(hydroxyethyl)diethylammonium, tri(hydroxyethyl)ethylammonium, hydroxyethyltriethylammonium, triethylmethylammonium, diethyldimethylammonium, triethylbutylammonium, triethylhexylammonium, tetraethylammonium, benzyltriethylammonium, and benzyltrimethylammonium.

Similarly, preferred compounds of formula I also include decyltriethylammonium, hydroxynonyltripropylammonium, dodecylbenzyldimethylammonium, dodecyltriethylammonium, dodecyl(hydroxyethyl)diethylammonium, octadecyltrimethylammonium, octadecyldi(hydroxyethyl)methylammonium, and dioctadecyldiethylammonium.

With regard to compounds of formula II, it is preferred that n be between 2 and 6, that the sum of carbon numbers in all of $R_5$, $R_6$, $R_7$, $R_8$, $R_9$, and $R_{10}$ be no greater than 20, and that each of $R_5$, $R_6$, $R_7$, $R_8$, $R_9$, and $R_{10}$ have between one and three carbon atoms. Thus, preferred compounds of formula H include alpha, omega-bis(trimethylammonium) hexane; alpha, omega-bis(triethylammonium) hexane; alpha, omega-bis(trimethylammonium) ethane; alpha, omega-bis(tripropylammonium) ethane; alpha, omega-bis(trimethylammonium)butane; and alpha, omega-bis(triethylammonium)butane.

The preferred compounds of formulae DIA and DIB are those in which R has between about 5 and 11 carbon atoms.

The amount of active employed will be that amount necessary to deliver a pharmaceutically or therapeutically effective amount to achieve the desired result at the site of application. In particular, an effective amount depends, inter alia, upon the particular active agent, the severity of the condition under treatment, and other factors. In general, the concentration of the active agents in the delivery systems can vary from as little as 0.001 up to 50 percent or higher, by weight of the delivery system. More typically, the active concentration is between about 0.01 and 10 wt percent of the delivery system. Skilled practitioners will be able to adjust the quantity of active in the delivery system.

It has been discovered that topical application of compounds of the formula:

$$[N\,(R_1)\,(R_2)\,(R_3)\,(R_4)]^+ \qquad (I)$$

wherein each $R^1$, $R^2$, $R^3$, and $R^4$ is straight chain or branched alkyl, alkylene, alkylaryl, saturated or unsaturated heterocyclic, saturated or unsaturated heterocyclic hydroxyalkyl, hydroxyalkyl, or hydroxyalkylene having up to about 20 carbon atoms; compounds of the formula $$[(R_5)\,(R_6)\,(R_7)\,N-(CH_{2n})-N\,(R_8)\,(R_9)\,(R_{10})]^{++} \qquad (II)$$

wherein each $R_5$, $R_6$, $R_7$, $R_8$, $R_9$, and $R_{10}$ is hydrogen or straight chain or branched alkyl, alkylene, alkylaryl, saturated or unsaturated heterocyclic, saturated or unsaturated heterocyclic hydroxyalkyl, hydroxyalkyl, or hydroxyalkylene having up to about 10 carbon atoms; and n is between 1 and about 10; compounds of the formulae

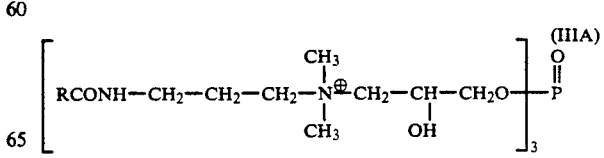

and

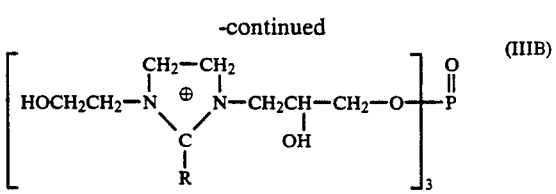

(IIIB)

wherein R is alkyl having from 5 to 17 carbon atoms; and 5-amino-1,3-bis(2-ethylhexyl)-5-methylhexahydropyrimidene and biologically acceptable salts thereof; and blends thereof, efficiently delivers the active agent.

Any delivery system may be utilized to deliver the active agent to the treatment site. Lotions, ointments, cremes, aerosols, and other topical application techniques are suitable. However, it has been discovered that a delivery system comprising chitosan derivatives and an active agent is unexpectedly efficient. The chitosan derivative forms a protective film over the application site. This protective film essentially ensures that the active agent is not removed from the application site (as by migration caused by perspiration). Further, the film is essentially imperceptible to the user. Thus, the preferred delivery system is not greasy, as are typical ointments and cremes, but instead is tactilely and visually pleasing.

Because each of the compounds to be thus delivered is soluble in water, the delivery system typically comprises an aqueous solution, and need not comprise a non-aqueous phase. However, non-aqueous components may be incorporated into the delivery system. If a nonaqueous component is introduced into the delivery system, an emulsion will be formed if a non-aqueous component is not soluble in the aqueous solution. However, preferably, the delivery system comprises solely components soluble in water.

There are several features which make the delivery systems of the present invention superior delivery vehicles. In the first instance, the delivery systems of this invention are substantive with hair, skin, and mucous membrane. Throughout the specification and claims, the term "substantive" means that there exists a cohesive interaction between the aminopolysaccharide derivative and a proteinaceous substrate, i.e., the hair, skin, or mucosa, to which the delivery system is applied. In the delivery systems of the present invention, substantivity typically is obtained by ensuring that the aminopolysaccharide derivative is cationically charged. The cationic charge is imparted by protonation or quaternization of the aminopolysaccharide. Incorporation of appropriate hydrophobic groups or combinations thereof may be used. Thus, the delivery systems of the present invention exhibit a cohesive interaction with the proteins of hair, skin, and mucosa.

Aminopolysaccharide derivatives, particularly chitosan derivatives, are good film-formers, i.e., a polymeric film is readily formed when an aqueous solution of a water-soluble aminopolysaccharide derivative is applied topically. Upon topical application of the delivery system of this invention, a polymeric film forms and serves as a reservoir from which the active is continuously delivered. The film also serves to protect the application site from insult or injury.

Cationically-charged chitosan derivatives exhibit substantive properties to keratin and other protein constituents of hair, skin, and mucosa. Thus, upon application of a cationic chitosan derivative to these tissues, the resulting film is bound to the substrate. This close relationship minimizes loss or migration of the film and the active agent. The system may also be applied to the skin or mucosa in the form of a preformed film, sponge, powder or other composite, as described below.

Application of an active- and aminopolysaccharide derivative-containing delivery system which forms a film provides uniform distribution of the active on the tissue and prevents migration or loss of the active from the site of application. The reservoir of active in the film helps to control the dosage at a constant level, thus controlling the rate of release. Also, chitosan derivatives which are free of naturally-associated proteins, heavy metals, and the like, are biocompatible and non-irritating to living tissue. These derivatives also do not elicit an inflammatory, allergic, or pyrogenic response in humans. In addition, the films these chitosan derivatives form on skin and mucosa are essentially imperceptible to the patient and cosmetically comfortable to wear. Further, the films are gas permeable.

The chitosan derivatives are also good humectants. Moisturization of the skin and mucous membranes enhances the absorption and permeation of most pharmaceutically and therapeutically active agents into those tissues. When these chitosan derivatives are applied to skin or mucous membranes, their humectant properties therefore enhance the absorption of the agents into these tissues.

As indicated above, there are two types of aminopolysaccharide derivatives which can be employed in the compositions of this invention. First are the chitosonium polymers. These chitosonium polymers are soluble in water and in mixtures of water and alcohol, readily form humectant films, and are substantive to skin and mucosa. Chitosonium polymer prepared by any method may be utilized in the subject invention. For example, these chitosonium polymers may be prepared by a number of known methods, including direct dissolution, spray drying, lyophilization, and the acid decrystallization process described in International Application Number PCT/US87/01246, published Dec. 17, 1987 as WO 87/07618.

Examples of chitosonium derivatives include those wherein one or more of the amino groups have been neutralized by acids, which may include: pyrrolidone carboxylic, acetic, tactic, glycolic, glyceric, mandelic, salicylic, benzoic, itaconic, malic, nicotinic, glutamic, aspartic, and the acid form of other amino acids such as N-acetyl methionine, N-acetyl tyrosine, N-acetyl glycine, N-benzoyl serine, and the like.

The second type of chitosan derivative included in this invention is covalent derivatives. These derivatives are prepared by the reaction of chitosan with one or more electrophilic reagents such as ethylene oxide, propylene oxide, glycidol, alkyl halides (from $C_1$ to $C_{24}$), glycidyl trialkylammonium salts (alkyl groups from $C_1$ to $C_{24}$), 3-chloro-2-hydroxypropyl ammonium salts, 1,3-propanesultone, haloacetates, succinic anhydride, maleic anhydride, carboxylic acyl halides, the N-carboxy-alpha-amino acid anhydrides, and the like. These chitosan derivatives are readily soluble in water, alcohol, water/alcohol mixtures, or, depending upon the structure of the derivative, may be soluble in ether, acetone, or ethyl acetate. These derivatives are good film formers, good humectants, and are substantive if cationic and/or hydrophobic groups are included in the polymer backbone.

Aminopolysaccharide derivatives suitable for use in the subject invention can be conveniently prepared by a method which comprises the steps of:

(a) forming a mixture of a pulverulent, partially deacetylated aminopolysaccharide and
  (1) a diluent medium in which the aminopolysaccharide is swellable but essentially insoluble; the medium comprised of:
    (i) an inert, water soluble, polar organic diluent in which the aminopolysaccharide is insoluble and the aminopolysaccharide derivative is insoluble; and
    (ii) at least one organic acid which is at least partially soluble in water, is sufficiently acidic to form the ammonium salt of the aminopolysaccharide and yet not sufficiently acidic to cause degradation of the aminopolysaccharide or derivative, and which is present in an amount sufficient to protonate the reactive sites of the deacetylated aminopolysaccharide; and
  (2) water in an amount up to about 65 weight percent of said medium;
(b) agitating the mixture at a temperature and for a period of time to effect at least partial decrystallization of the aminopolysaccharide to form an aminopolysaccharide derivative; and
(c) recovering the aminopolysaccharide derivative from the mixture.

As described above, a variety of derivatives of decrystallized aminopolysaccharides, such as chitosan, can be prepared. These derivatives can be ionic compositions (salts) or covalent compositions.

To prepare covalent chitosan derivatives such as esters, amides, and ethers, the swollen, decrystallized slurry of the chitosan salt prepared by the aforementioned method, is causticized with a stoichiometric excess of a base such as sodium hydroxide and then reacted with an electrophile, such as ethylene oxide, propylene oxide, glycidol, 1,2-epoxy dodecane, chloroacetic acid, succinic anhydride, and the like.

To prepare ionic derivatives in the form of salts of chitosan, the acid used in the decrystallization step is chosen to provide the desired functional group and both decrystallization and derivatization, i.e. salt formation, is accomplished simultaneously. Alternatively, the organic acid utilized in the decrystallization step can be selenited so that the chitosan is not only decrystallized but the salt is obtained containing the desired organic function present in the acid employed.

The decrystallization method described herein differs from other known methods in several respects. First, the acid decrystallization process does not involve dissolution of aminopolysaccharide, such as chitosan, in an aqueous medium. Since chitosan is a very rigid molecule, only a small quantity of chitosan having a moderately high molecular weight (between about 20,000 and greater than 1 million) can be rendered water soluble before the solution becomes too viscous to be easily handled. If the solution is further diluted to reduce the viscosity, the concentration of chitosan is reduced even further. The dilute nature of such a solution makes chemical reaction to derivatize the molecule inefficient and economically unattractive.

For example, literature currently available from a company engaged in the commercial sale of chitosan in the United States indicates that chitosan is soluble in solutions of most acids, particularly organic acids such as formic acid, malic, tartaric, citric, adipic, and the like. It is further indicated that in order to make a one percent solution of chitosan in water, chitosan is mixed with water and then an equal volume of acid solution is added. For concentrated solutions of chitosan, which are indicated in the literature reference to be from about 2 to 4 percent by weight, an equal weight of acid to that of the chitosan is employed. With inorganic acids such as hydrochloric or nitric acids chitosan is soluble within the range of 0.15 to 1.1 percent acid by weight. Chitosan is not soluble in sulfuric acid and has only marginal solubility in phosphoric acid at concentrations below 0.5 percent.

Thus, the decrystallization method described herein provides the only method known to the inventors whereby aminopolysaccharides are economically decrystallized and derivatized, and recovered, by a simple and efficient process.

A variety of acids can be used in the decrystallization process. It is, of course, necessary that the acid be at least partially soluble in water or hydrophilic media, be sufficiently acidic to form the ammonium salt of the aminopolysaccharide and yet not sufficiently acidic to cause hydrolysis of the aminopolysaccharide or derivative, and be present in an amount sufficient to protonate the reactive sites of the deacetylated aminopolysaccharides.

Such acids can be represented by the formula:

$$R\text{-}(COOH)_n$$

wherein n has a value of 1 or 2 and R represents a monovalent or divalent organic radical composed of carbon, hydrogen, and optionally at least one moiety selected from the group consisting of oxygen, nitrogen, and sulfur. Combinations of such acids also may be utilized. Preferred acids are the mono- and di-carboxylic acids composed of carbon, hydrogen, oxygen, and nitrogen, which are at least partially water soluble and biologically and/or pharmaceutically acceptable for use in the delivery systems of the present invention.

Accordingly, a wide variety of acids can be employed to simultaneously decrystallize chitosan and provide derivatives suitably utilized in the present invention. Such acids, in addition to those previously identified, include formic, acetic, N-acetylglycine, acetysalicylic, fumaric, gallic, glycolic, iminodiacetic, itaconic, DL-lactic, maleic, DL-malic, methaerylic, 2-pyrrolidone-5-carboxylic, salicylic, succinamic, succinic, ascorbic, aspartic, adipic, glutamic, glutaric, malonic, nicotinic, pyruvic, sulfonyldiacetic, thiodiacetic, and thioglycolic acids.

The medium employed in the decrystallization of the chitosan is a diluent system combining water and an organic compound. Organic compounds which are useful in this diluent system are those which are water soluble, in which the aminopolysaccharide is insoluble, and in which the aminopolysaccharide derivative is insoluble. Organic compounds suitably employed include acetone, methanol, ethanol, n-propanol, isopropanol, tertiary butyl alcohol, acetonitrile, tetrahydrofuran, dioxane, 2-ethoxyethanol, dimethoxyethane, and the like.

The second component of the diluent medium is water, which is present in an amount up to about 65 weight percent of the total medium, i.e., the total of the water plus the organic compound. In practice, optimum results are obtained when the diluent medium contains from about 30 to about 45 weight percent water and more preferably about 40 weight percent.

In contrast to other methods, the decrystallization described herein avoids formation of a chitosan solution. Rather chitosan is caused to swell and it is unnecessary to form viscous solutions which contain only a few percent chitosan.

The sequence of mixing the diluent medium and the deacetylated chitosan is not critical. However, it has been observed that excellent results are obtained if the diluent medium is prepared from the water and organic compound together with the acid and then the chitosan added.

Chitosan, which is a deacetylated form of chitin, has a very rigid structure, as illustrated in the following formula:

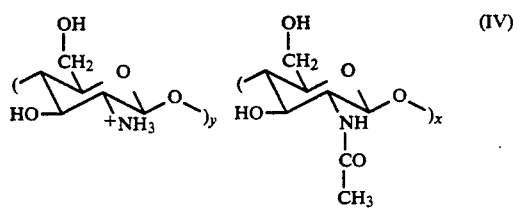

wherein x is between 0 and 0.5; y is between 0.5 and 1; and $x+y=1$. The degree of deacetylation and the molecular weight which occurs in natural chitin depends upon the species, e.g., shellfish from which the chitin is obtained and the method by which it is purified. In chitosan, typical ranges are y is between about 0.5 and 0.9 and x is between about 0.1 and 0.5. Dissolution of chitosan having a low degree of deacylation in acid solution yields a very viscous product with a significant insoluble fragment.

For chitosan salts or derivatives to be soluble in water, they should be prepared from starting materials which have a relatively large number of free primary amine groups, i.e., y should be larger than about 0.5. Preferably, the degree of deacetylation of chitosan used herein is in excess of 60 percent, and more preferably in excess of 70 percent. The molecular weight range of chitosan employed in the present invention can range from about 5000 to over a million and more preferably from about 10,000 to about 500,000. Particularly preferred is chitosan having a molecular weight of from about 20,000 to about 250,000.

The viscosity of a chitosan derivative solution of given concentration increases as the molecular weight of the chitosan increases. Thus, in solutions containing one percent chitosonium derivative which has viscosities of 5 cP and 500 cP, respectively, the higher-viscosity solution has a higher molecular weight. For the purposes of this invention, lower-viscosity solutions are preferred. Thus, typically, the viscosity of a one percent solution of chitosonium derivative is less than about 700 and preferably is less than about 100 cP, more preferably less than about 25 cP, and most preferably less than about 10 cP.

The above-described mono- and di-carboxylic acids or other combinations can be employed in the preparation of derivatives of chitosan useful in this invention. Thus, derivatives of chitosan suitable for use in the present invention include chitosan salts of carboxylic acids (R'COOH) having the formula:

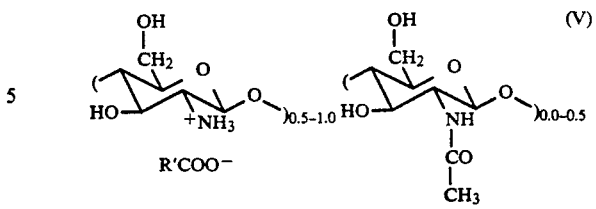

example, pyrrolidone carboxylic acid (PCA) is an effective moisturizing agent which has a low order of irritation. Chitosonium pyrrolidone carboxylate has a large number of useful applications such as topical medical formulations. The pyrrolidone carboxylic acid salt of chitosan is useful in delivery systems of the present invention. Such a polymer is prepared by reacting a finely ground slurry of chitosan with PCA in a polar solvent such as aqueous isopropanol, or other suitable solvent that will dissolve PCA and swell the chitosan pyrrolidone carboxylic acid salt, but not dissolve it.

Other chitosan derivatives, e.g., salts of other organic acids that are soluble in polar organic solvents such as isopropanol, may be made by this decrystallization process. For example, glycolic acid or lactic acid in aqueous ethanol can be reacted with chitosan to give the glycolate salt or lactate salt, which also are useful as delivery systems.

When free of its naturally associated proteins, chitin or chitosan is not antigenic to human tissue, and may be used on or inserted under the skin, or placed in contact with body fluids without harm. Chitin in the body is slowly attacked by lysozyme and is absorbed. In addition, chitin and chitosan may be safely ingested by humans, for example, common foods such as bread, beer, wine, shrimp, crabs, and mushrooms all contain some chitin.

In addition to the chitosonium polymers and covalent chitosan derivatives prepared as described above, the delivery systems of the present invention can be comprised of chitosan derivatives prepared by known methods.

Chitosonium polymers suitable for use in the present invention include salts of chitosan prepared with the following acids:
Acetic
N-Acetyl-L-cysteine
N-Acetyl glycine
Acetylsalicylic
Adipic
L-Aspartic
Citric
Fumaric
2-Furoic
Gallic
L-Glutamic
Glutaric
Glycolic
Hydrochloric
4-Hydroxybenzoic
Iminodiacetic
Itaconic
3-Ketoglutaric
DL-Lactic
Maleic
DL-Malic
Malonic
Nicotinic (Niacin)

2,3-Pyridinedicarboxylic
2-Pyrrolidone-5-carboxylic
Pyruvic
Salicyclic
Succinamic
Succinic
Sulfanilic
Sulfonyldiacetic
L-Tartaric
Thioacetic
Thiolactic
Vanillic Combinations of these acids also are suitable.

These salts are readily soluble in water at room temperature, except for the malate, maleate, itaconate, salicylate, fumarate, and succinate salts, which require heating to about 75° C. to effect dissolution, after which they remain soluble. The products from the reaction of acrylic, citric, gallic, 4-hydroxybenzoic, and vanillic acids, when used alone, are only slightly soluble in water, because the reaction by which the derivative is formed has limited efficiency.

Chitosan derivatives which can be prepared by the above process include, but are not limited to, chitosonium pyrrolidone carboxylate, chitosonium itaconate, chitosonium niacinate, chitosonium salicylate, chitosonium lactate, chitosonium formate, chitosonium acetate, chitosonium gallate, chitosonium glutamate, chitosonium maleate, chitosonium succinamate, chitosonium aspartate, chitosonium glycolate, and combinations thereof. Each is suitable for use in the subject invention.

In general, the amount of chitosan derivative employed in the compositions of this invention will vary depending upon the particular pharmaceutical or therapeutic active being delivered, whether diluent is present, the type of additives, and the like. In practice, however, it has been found that a concentration of the chitosan derivative in the composition can range up to about 20, preferably between about 0.05 and 10, weight percent, based on the total weight of the composition.

Moisturizing agents such as lactic acid, pyrrolidone carboxylic acid, glycolic acid, glycerine, propylene glycol, sorbitol, other alphahydroxy carboxylic acids, and various salts of these esters and salts, may also be incorporated into delivery systems of the invention.

If desired, the delivery systems of this invention can contain one or more pharmaceutically acceptable diluents or vehicles in addition to the chitosan derivative and the active component. In many instances, the chitosan derivative itself can be about 0.5 to about 20 weight percent of the system with the remainder being diluent and optionally, other additives. Suitable diluents include among others, water, ethanol, aqueous ethanol, isopropanol, glycerine, dimethylether, polyethylene glycol, ethoxylated or propoxylated glucose, sorbitol derivatives, and the like.

Additives for the enhanced percutaneous absorption of various pharmaceutical or therapeutic actives also may be utilized. Such percutaneous enhancers include propylene glycol, glycerol, urea, diethyl sebecate, sorbitan ethoxylates, nicotinate esters (such as hexyl nicotinate), oleic acid, pyrrolidone carboxylate esters, (such as dodecyl pyrrolidone carboxylate), N-methyl pyrrolidone, N,N-diethyl-m-toluamide, dimethyl sulfoxide, decyl methyl sulfoxide, alkyl methyl sulfoxides, N,N-dimethyl formamide, cis-11-octadecenoic acid, 1-dodecylazacycloheptan-2-one, and 1,3-dioxacyclopentane or 1,2-dioxacyclohexane containing at least one aliphatic group of four to eighteen carbon atoms.

The delivery systems of the present invention are particularly efficient for delivery of the water-soluble quaternary and related compounds described herein. The chitosan salt forms a film over the application site, ensuring that the active agent does not migrate and is not removed from the site, e.g., by perspiration or contact with clothing. The excellent site protection afforded by the chitosan film affords the opportunity to deliver to a site a precisely-measured quantity of active agent per application. Therefore, instead of requiring a dosage quantity calculated with the assumption that some of the active agent will migrate, as typically is required by known delivery systems, the delivery system of the present invention delivers a dosage more precisely. Thus, better control over the dosage reduces the possibility of overdosing and provides several benefits, including increased consumer acceptance and improved treatment derived, inter alia, from an easily understood and executed treatment schedule and treatment which produces fewer unpleasant side effects. Further, the delivery system of the invention affords an even delivery rate over a long period.

Delivery systems of the invention can comprise oil-in-water emulsions, if it is found desirable to have an oil phase. Oil-in-water emulsions feel relatively "non-greasy" when applied, whereas water-in-oil emulsions tend to have a greasy or oily feel. Therefore, oil-in-water emulsions are preferred by consumers.

Emulsion-type delivery systems of the invention are made by the "direct" method or by the "inversion" method. In the "direct" method, the oil phase is dispersed into the continuous aqueous phase to form the oil-in-water emulsion directly. An oil-in-water emulsion is made by the "inversion" method by emulsifying the aqueous phase into a continuous oil phase. At first, a water-in-oil emulsion is formed, but, as the quantity of aqueous phase is increased, the emulsion becomes "inverted" and forms an oil-in-water emulsion. Either preparation method can be used to prepare emulsion-type delivery systems of the invention.

When the active agents described herein are delivered by the delivery system of the invention, care should be taken to select the salt or counter-ion or otherwise provide the solution with a pH which is not only suitable for topical application but also does not interfere with the aminopolysaccharide derivative. For example, some of the chitosan salts precipitate as chitosan if the pH exceeds about 5.5. Not only might precipitated chitosan be looked upon by a consumer unfavorably, as it may be tactilely unpleasant, but also the protective film may not form.

In practice, the delivery systems of the invention are readily formulated by mixing an active agent, or an aqueous solution of an active agent, with a solution or suspension of the chitosan derivative. Alternatively, dry chitosan derivative can be dissolved or suspended in an aqueous solution of an active agent. Indeed, any method of forming a solution may be utilized. If an oil phase is present, an emulsion is formed. A suitable emulsifier may be used. Other adjuvant ingredients such as glycerine, propylene glycol, sorbitol, preservatives, stearic acid, cetyl alcohol, other high molecular weight alcohols, surfactants, menthol, eucalyptus oil, other essential oils, fragrances, penetration enhancers, and the like to give stable delivery systems, such as cremes, ointments, lotions, and aerosols, may also be included.

Alternatively, solutions or mixtures of the actives with the chitosan derivatives may be fabricated into films, rods, sheets, sponges, or fibers for use as suppositories, medicated sutures, medicated sheets, medicated bandages, patches, and the like.

The following examples are intended to further illustrate the invention, not to limit it in any way. The scope of the invention is limited only to the scope of the appended claims.

EXAMPLES

Throughout the Examples, all parts are parts by weight, unless otherwise identified.

Example 1

A solution of 3.18 parts chitosan lactate (viscosity of I percent solution about 5 cP) and 77 parts water was prepared. Then, 4.22 parts tetraethylammonium chloride was added and mixed until completely in solution.

This solution was applied 3 times per day in a quantity sufficient to deliver about 1 mg active agent (tetraethylammonium ion) per kg of body weight per application to areas of the skin of a guinea pig presenting symptoms of diseases caused by herpes virus.

The subject experienced remission of skin eruptions to which the solution of the invention was applied and other symptoms of infection by herpes simplex virus, type 2.

Example 2

A solution is made by the method described in Example 1 utilizing a chitosan nicotinate solution. The delivery system provides the same beneficial effects as does the solution of Example 1, and further provides vasodilation.

Example 3

A solution was prepared by the method described in Example 1, except that the viscosity of the one percent chitosan lactate solution was about 500 cP. Application to guinea pig skin ameliorated the skin eruptions less effectively than the solution of Example 1.

Example 4

A chitosan solution is prepared by dissolving 3.2 parts chitosonium lactate (as described in Example 1) in 52 parts purified water. To this solution is added 4 parts of 5-amino-1,3-bis(2-ethylhexyl)-5-methylhexahydropyrimidene which has been dissolved in 25 parts propylene glycol.

The resulting delivery system is applied to a substrate containing Staphylococcus Aureus bacteria. Subsequent to application, the bacteria concentration is significantly reduced.

Example 5

A solution of chitosan nicotinate is prepared by dissolving 5 parts of chitosan nicotinate in 85 parts water. To this solution is added 10 parts alpha, omega-bis(-trimethylammonium) hexane chloride.

The resulting delivery system is applied in the form of a film patch to provide antihypertensive effect.

Example 6

A solution is prepared by dissolving 3.5 parts chitosan lactate and 5.0 parts tetraethylammonium chloride in 86.5 parts purified water which is heated to 75° C. An oil phase is prepared by blending 4.5 parts Promulgen D (cetearyl alcohol, a mixture of cetyl and stearyl alcohols, with ceteareth 20) and 0.5 parts glycerol monosterate and heating to 75° C.

The two phases then are mixed with vigorous agitation to form an emulsion, then cooled with agitation. The emulsion is applied to skin lesions resulting from herpes simplex virus in a quantity sufficient to deliver 1 mg per kg of body weight.

Example 7

A solution is prepared by dissolving 3.5 parts of medium molecular weight chitosan lactate in 96.5 parts purified water. Then, 5 parts tetraethylammonium chloride is added, and the mixture is stirred until the tetraethylammonium chloride is dissolved.

The solution is applied to lesions on the skin (herpes virus symptoms) and alleviates pain and reduces the size of the lesions. The quantity which is applied is sufficient to deliver 1 mg per kg of body weight three times daily.

Example 8

A solution of low molecular weight chitosan lactate was prepared by mixing 7.0 parts chitosan lactate with 93.0 parts purified water. A solution of 10 parts tetraethylammonium chloride dissolved in 90 parts purified water was prepared and was mixed into the chitosan lactate solution.

The solution is applied three times daily to provide 1.5 mg per kg of body weight per application. The treatment ameliorates the symptoms.

Although preferred embodiments of the invention have been discussed herein, those skilled in the art will appreciate that changes and modifications may be made without departing from the spirit of the invention, as defined in and limited only by the scope of the appended claims.

We claim:

1. A biocompatible, substantive, film-forming system for the delivery of pharmaceutically or therapeutically active agents to a desired topical site of a subject or host consisting essentially of
   (a) at least one aminopolysaccharide derivative selected from the group consisting of chitosonium polymers and covalent chitosan derivatives, and
   (b) a pharmaceutically or therapeutically active ingredient selected from the group consisting of compounds of of the formula:

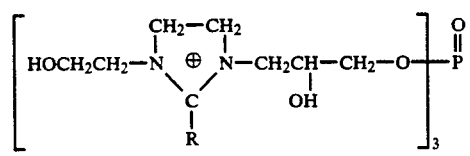

wherein R has between 5 and 11 carbon atoms.

* * * * *